(12) United States Patent
Corey

(10) Patent No.: US 10,074,260 B2
(45) Date of Patent: Sep. 11, 2018

(54) METHOD AND SYSTEM FOR SIGNALING RESPONSIVE TO SENSING CONTAMINATION IN A SUCTION REGULATOR DEVICE

(71) Applicant: Amico Patient Care Corporation, Richmond Hill (CA)

(72) Inventor: Sarah Corey, Uxbridge (CA)

(73) Assignee: Amico Patient Care Corporation, Richmond Hill (CA)

( * ) Notice: Subject to any disclaimer, the term of this patent is extended or adjusted under 35 U.S.C. 154(b) by 177 days.

(21) Appl. No.: 14/918,293

(22) Filed: Oct. 20, 2015

(65) Prior Publication Data

US 2016/0109379 A1   Apr. 21, 2016

Related U.S. Application Data

(60) Provisional application No. 62/066,013, filed on Oct. 20, 2014, provisional application No. 62/159,807, filed on May 11, 2015.

(51) Int. Cl.

| | |
|---|---|
| *G08B 21/18* | (2006.01) |
| *G01N 21/01* | (2006.01) |
| *A61M 1/00* | (2006.01) |
| *G01N 21/53* | (2006.01) |
| *G01N 21/94* | (2006.01) |

(52) U.S. Cl.
CPC .......... *G08B 21/18* (2013.01); *A61M 1/0031* (2013.01); *A61M 1/0049* (2013.01); *G01N 21/01* (2013.01); *A61M 2205/15* (2013.01); *A61M 2205/18* (2013.01); *A61M 2205/3306* (2013.01); *A61M 2205/584* (2013.01); *A61M 2205/8206* (2013.01); *G01N 21/534* (2013.01); *G01N 21/94* (2013.01)

(58) Field of Classification Search
CPC ... G08B 21/18; A61M 1/0031; A61M 1/0049; A61M 2205/15; A61M 2205/18; A61M 2205/3306; A61M 2205/584; A61M 2205/8206; G01N 21/01; G01N 21/534; G01N 21/94
USPC ................................. 73/37; 604/45; 433/95
See application file for complete search history.

(56) References Cited

U.S. PATENT DOCUMENTS

| | | | |
|---|---|---|---|
| 4,988,336 A | 1/1991 | Kohn | |
| 5,467,501 A * | 11/1995 | Sepke | A47L 9/2847 15/324 |
| 5,622,163 A * | 4/1997 | Jewett | A61M 15/009 128/200.19 |
| D412,984 S | 8/1999 | Cover et al. | |
| 5,944,703 A | 8/1999 | Dixon et al. | |
| 6,338,728 B1 | 1/2002 | Valerio et al. | |
| 6,749,592 B2 | 6/2004 | Lord | |
| 6,960,190 B2 | 11/2005 | Stinson | |
| 7,131,966 B1 * | 11/2006 | Tamari | A61M 1/3621 128/DIG. 3 |
| 7,143,773 B2 | 12/2006 | Stinson | |
| 7,686,785 B2 | 3/2010 | Boehringer et al. | |
| 8,518,017 B2 | 8/2013 | Caluori | |

(Continued)

*Primary Examiner* — Manish S Shah
*Assistant Examiner* — Suman K Nath
(74) *Attorney, Agent, or Firm* — Ridout & Maybee LLP

(57) ABSTRACT

The present application relates generally to a suction regulator device and, more specifically, to a method and system for signaling responsive to sensing that the suction regulator device has become contaminated.

14 Claims, 4 Drawing Sheets

(56) References Cited

U.S. PATENT DOCUMENTS

| | | |
|---|---|---|
| 2003/0204129 A1 | 10/2003 | Jahns et al. |
| 2005/0017021 A1 | 1/2005 | Jahns et al. |
| 2005/0103388 A1 | 5/2005 | Stinson |
| 2007/0012357 A1 | 1/2007 | Stinson |
| 2007/0135779 A1 | 6/2007 | Lalomia et al. |
| 2007/0177136 A1* | 8/2007 | Nakano .................. G01N 21/94 356/237.2 |
| 2008/0009679 A1 | 1/2008 | Jahns et al. |
| 2008/0015504 A1* | 1/2008 | Boehringer ......... A61M 1/0031 604/119 |
| 2009/0082741 A1 | 3/2009 | Hu |
| 2009/0272444 A1 | 11/2009 | Clementi et al. |
| 2010/0049152 A1 | 2/2010 | Lalomia et al. |
| 2010/0058791 A1 | 3/2010 | Quesada Saborio |
| 2010/0145290 A1 | 6/2010 | Boehringer et al. |
| 2010/0198175 A1 | 8/2010 | Rosero |
| 2011/0048106 A1 | 3/2011 | Zawacki et al. |
| 2011/0052480 A1 | 3/2011 | Martens et al. |
| 2011/0067779 A1 | 3/2011 | Gray |
| 2011/0072783 A1 | 3/2011 | Hepburn et al. |
| 2011/0072784 A1 | 3/2011 | Hepburn et al. |
| 2011/0072787 A1 | 3/2011 | Hubbard et al. |
| 2011/0072794 A1 | 3/2011 | Van Nieuwstadt et al. |
| 2011/0072795 A1 | 3/2011 | Kerns et al. |
| 2011/0072803 A1 | 3/2011 | Van Nieuwstadt et al. |
| 2011/0072804 A1 | 3/2011 | Van Nieuwstadt et al. |
| 2011/0073070 A1 | 3/2011 | Ruhland et al. |
| 2011/0073088 A1 | 3/2011 | Hubbard et al. |
| 2011/0116975 A1 | 5/2011 | Persinger et al. |
| 2011/0120062 A1 | 5/2011 | Leu et al. |
| 2011/0129388 A1 | 6/2011 | Alarid et al. |
| 2011/0132325 A1 | 6/2011 | Peters et al. |
| 2011/0132489 A1 | 6/2011 | Leu et al. |
| 2011/0282326 A1 | 11/2011 | Krupa |
| 2012/0017903 A1* | 1/2012 | von Schuckmann ........................ A61M 15/0065 128/203.15 |
| 2012/0123322 A1* | 5/2012 | Scarpaci .................. G01V 8/20 604/29 |
| 2012/0174564 A1 | 7/2012 | Zawacki et al. |
| 2012/0174892 A1 | 7/2012 | Ruhland et al. |
| 2012/0210939 A1 | 8/2012 | Sandberg et al. |
| 2012/0238972 A1 | 9/2012 | Karpowicz et al. |
| 2012/0245865 A1 | 9/2012 | Caso et al. |
| 2012/0281035 A1 | 11/2012 | Uptergrove |
| 2012/0294781 A1 | 11/2012 | Taylor et al. |
| 2012/0323433 A1 | 12/2012 | Rollinger et al. |
| 2013/0019744 A1 | 1/2013 | Hu |
| 2013/0069783 A1 | 3/2013 | Caso et al. |
| 2013/0072786 A1 | 3/2013 | Keogh et al. |
| 2013/0079917 A1 | 3/2013 | Deppermann et al. |
| 2013/0106932 A1 | 5/2013 | Uptergrove |
| 2013/0133559 A1 | 5/2013 | Salmento |
| 2013/0255353 A1 | 10/2013 | Zawacki et al. |
| 2013/0267919 A1 | 10/2013 | Caso et al. |
| 2013/0283898 A1 | 10/2013 | Rollinger et al. |
| 2013/0296879 A1 | 11/2013 | Lazeroms et al. |
| 2013/0306040 A1 | 11/2013 | Yamada |
| 2014/0052082 A1 | 2/2014 | Krupa et al. |
| 2014/0086822 A1 | 3/2014 | Martens et al. |
| 2014/0221823 A1 | 8/2014 | Keogh et al. |
| 2014/0230366 A1 | 8/2014 | Leu et al. |
| 2014/0254305 A1 | 9/2014 | Caso et al. |
| 2014/0305881 A1 | 10/2014 | Alarid et al. |
| 2014/0338529 A1 | 11/2014 | Reasoner et al. |
| 2014/0352670 A1 | 12/2014 | Surnilla et al. |
| 2014/0356227 A1 | 12/2014 | Mclean et al. |
| 2015/0053190 A1 | 2/2015 | Hubbard et al. |
| 2015/0059337 A1 | 3/2015 | Wang et al. |
| 2015/0065969 A1 | 3/2015 | Stinson |
| 2015/0088068 A1 | 3/2015 | Moulden et al. |
| 2015/0158288 A1 | 6/2015 | Gemelli |
| 2015/0224237 A1 | 8/2015 | Reasoner et al. |
| 2015/0250130 A1 | 9/2015 | Bahlenberg |
| 2015/0369722 A1* | 12/2015 | Donner .............. G01N 15/1459 73/864.72 |

* cited by examiner

METHOD AND SYSTEM FOR SIGNALING RESPONSIVE TO SENSING CONTAMINATION IN A SUCTION REGULATOR DEVICE

CROSS-REFERENCE TO RELATED APPLICATIONS

The present application claims priority to U.S. Provisional Patent Application No. 62/066,013, filed Oct. 20, 2014. The present application claims priority to U.S. Provisional Patent Application No. 62/159,807, filed May 11, 2015. The contents of both documents are hereby incorporated herein by reference.

FIELD

The present application relates generally to a suction regulator device and, more specifically, to a method and system for signaling responsive to sensing that the suction regulator device has become contaminated.

BACKGROUND

Various models of suction regulator devices exist in the market. Each of the various models share similar features, while some models possess unique capabilities.

A suction regulator device is a regulation means for controlling the vacuum and flow of the vacuum source from a vacuum terminal of a vacuum supply system. The suction regulator device, together with a liquid collection bottle for clinical liquid suction, forms a suction system.

BRIEF DESCRIPTION OF THE DRAWINGS

Reference will now be made, by way of example, to the accompanying drawings which show example implementations; and in which.

DETAILED DESCRIPTION

Figure 1:
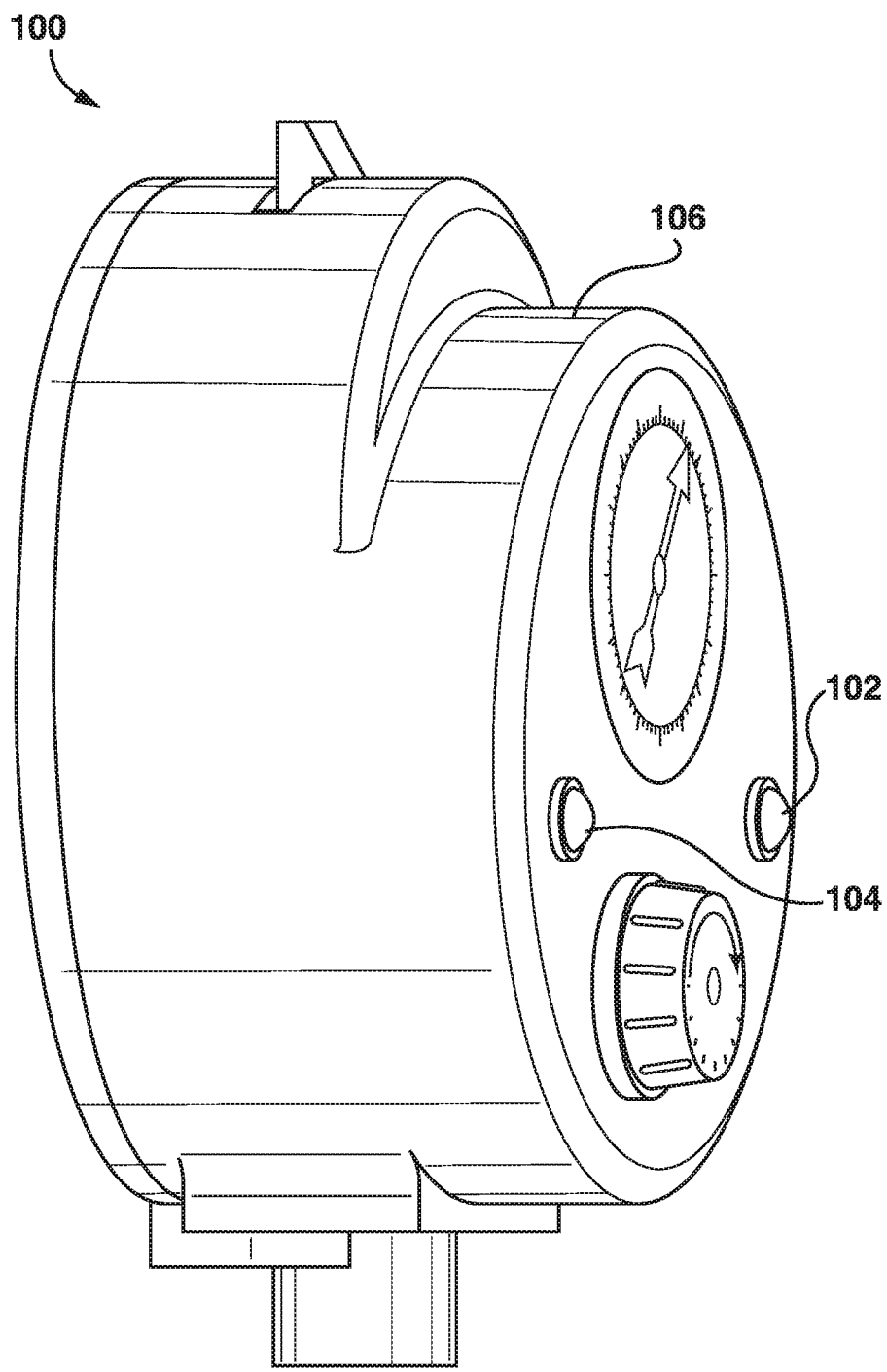
FIG. 1 illustrates, in perspective view, a suction regulator device.

The present application relates generally to a suction regulator device and, more specifically, to a method and system for signaling responsive to sensing that the suction regulator device has become contaminated.

According to an aspect of the present disclosure, there is provided a method of signaling responsive to sensing contamination of a suction regulator device. The method includes receiving, from a sensor, an indication, determining, from the indication, that the suction regulator device has been contaminated and responsive to the determining, transmitting, to an alerting device, an instruction to generate an alert indicative of the contamination. In other aspects of the present application, a suction regulator device is provided with a processor for carrying out this method and a computer readable medium is provided for adapting a processor in a suction regulator device to carry out this method.

According to another aspect of the present disclosure, there is provided a suction regulator device. The suction regulator device includes a molded layer defining an entry point, a plurality of channels and a pathway that connects the entry point to the channels and an opaque cover adapted to cover the molded layer, the opaque cover defining an aperture, the aperture closed with a transparent window, the window located proximate to the pathway.

According to a further aspect of the present disclosure, there is provided a suction regulator device. The suction regulator device includes a molded layer defining an entry point, a plurality of channels and a pathway that connects the entry point to the channels and an opaque cover adapted to cover the molded layer, the opaque cover defining an aperture, the aperture closed with a transparent window located proximate to the channels.

According to a still further aspect of the present disclosure, there is provided a method of retrofitting a suction regulator device, the suction regulator device having a layer defining an entry point, a plurality of channels and a pathway that connects the entry point to the channels. The method includes installing a sensor proximate the pathway, installing an alerting device and installing a processor. The processor being adapted to receive, from the sensor, an indication, determine, from the indication, that the suction regulator device has been contaminated and transmit, to the alerting device, an instruction to generate an alert indicative of the contamination.

According to an even further aspect of the present disclosure, there is provided a method of retrofitting a suction regulator device, the suction regulator device having a layer defining an entry point, a plurality of channels and a pathway that connects the entry point to the channels, the suction regulator device also having a first cover adapted to cover the layer. The method includes removing the first cover and installing a second cover in place of the first cover, the second cover defining an aperture, the aperture closed with a transparent window, the window located proximate to the pathway.

According to a still even further aspect of the present disclosure, there is provided a method of retrofitting a suction regulator device, the suction regulator device having a layer defining an entry point, a plurality of channels and a pathway that connects the entry point to the channels, the suction regulator device also having a first cover adapted to cover the layer. The method including removing the first cover and installing a second cover in place of the first cover, the second cover defining an aperture, the aperture closed with a transparent window, the window located proximate to the channels.

According to a still even further aspect of the present disclosure, there is provided a suction regulator device. The suction regulator device includes a base, a cover and a layer defining an entry point, a plurality of channels and a pathway that connects the entry point to the channels. The base and the cover enclose the layer. The base comprises a material that is at least partially transparent, thereby allowing viewing of the channels and any contaminants that may have entered into the channels.

According to a still even further aspect of the present disclosure, there is provided a method of retrofitting an existing vacuum system, the vacuum system having a vacuum source, a vacuum line communication between vacuum source and patient cavity and a suction regulator within the vacuum line. The method includes installing at least one sensor within a pathway along the vacuum line and installing an alerting device. The method further includes installing a circuit adapted to receive, from the sensor, an indication, determine, from the indication, that the vacuum line has been contaminated and transmit, to the alerting device, an instruction to generate an alert of the contamination.

Other aspects and features of the present disclosure will become apparent to those of ordinary skill in the art upon review of the following description of specific implementations of the disclosure in conjunction with the accompanying figures.

FIG. 1 illustrates, in perspective view, a suction regulator device 100. The suction regulator device 100 includes, among other features, a cover 106, a contamination indicator light 102 and a low battery indicator light 104.

Figure 2:
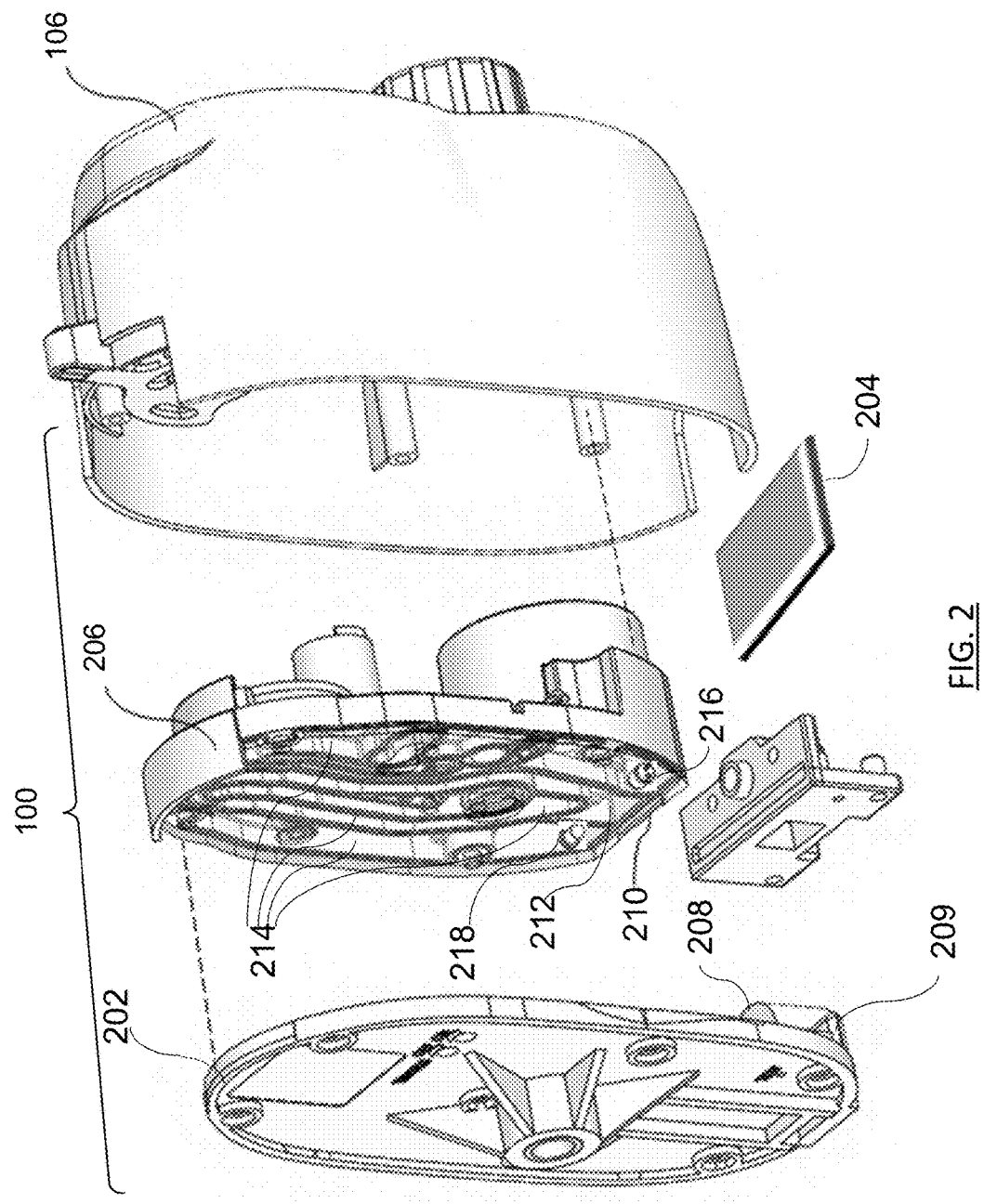
FIG. 2 illustrates, in exploded perspective view, elements of the suction regulator device of FIG. 1.

FIG. 2 illustrates, in exploded perspective view, elements of the suction regulator device 100. The suction regulator device 100 includes a base 202, a circuit board 204 and a molded layer 206. The base 202 has a generally flat structure except for a flanged portion 208 at an end of the suction regulator device 100 that may be connected to a clinical apparatus that requires suction. The flanged portion 208 defines an aperture 209. The opposite end of the suction regulator device 100 may be connected to a vacuum terminal of a vacuum supply system (not shown).

The molded layer 206 defines a plurality of channels 214. The molded layer 206 also defines an entry point 210. When the suction regulator device 100 is properly assembled, the location of the entry point 210 coincides with the location of the aperture 209 in the flange 208 of the base 202. Between the entry point 210 and the channels 214, the molded layer 206 defines a pathway 212. A light source 218 may be located on one side of the pathway 212. A corresponding light sensor 216 may be located on an opposite side of the pathway 212. The light source 218 may be, for but two examples, an incandescent bulb or a light emitting diode.

The pathway 212 may contain features designed to collect contaminants. Such features may, for example, be located in the pathway 212 proximate to the light sensor 216. Furthermore, an optical filter (not shown) may be placed between the light source 218 and the light sensor 216. The optical filter may, for example, comprise a polarizing filter.

The circuit board 204 may house a processor (not shown) and a memory (not shown).

In the models of suction regulator devices that are currently available, it is up to the users to decide whether to send a suction regulator device to the user's "cleaning" department for cleaning or sanitizing. Since each suction regulator device is a closed system, there is currently no method by which to identify whether a given suction regulator device is contaminated. As will be readily understood, contamination may take many forms. In general, contamination may involve presence, in the suction regulator device 100, of particles and/or aspirates.

In overview, by utilizing various unique features of the suction regulator device 100 of FIG. 1, a user may learn that a foreign body has passed into the suction regulator device 100, that is, that the suction regulator device 100 has become contaminated. Responsive to learning that the suction regulator device 100 has become contaminated, it is expected that the user will understand that the suction regulator device 100 should be taken out of use. Perhaps the user will, responsive to learning that the suction regulator device 100 has become contaminated, send the suction regulator device 100 to a cleaning department.

Figure 3:
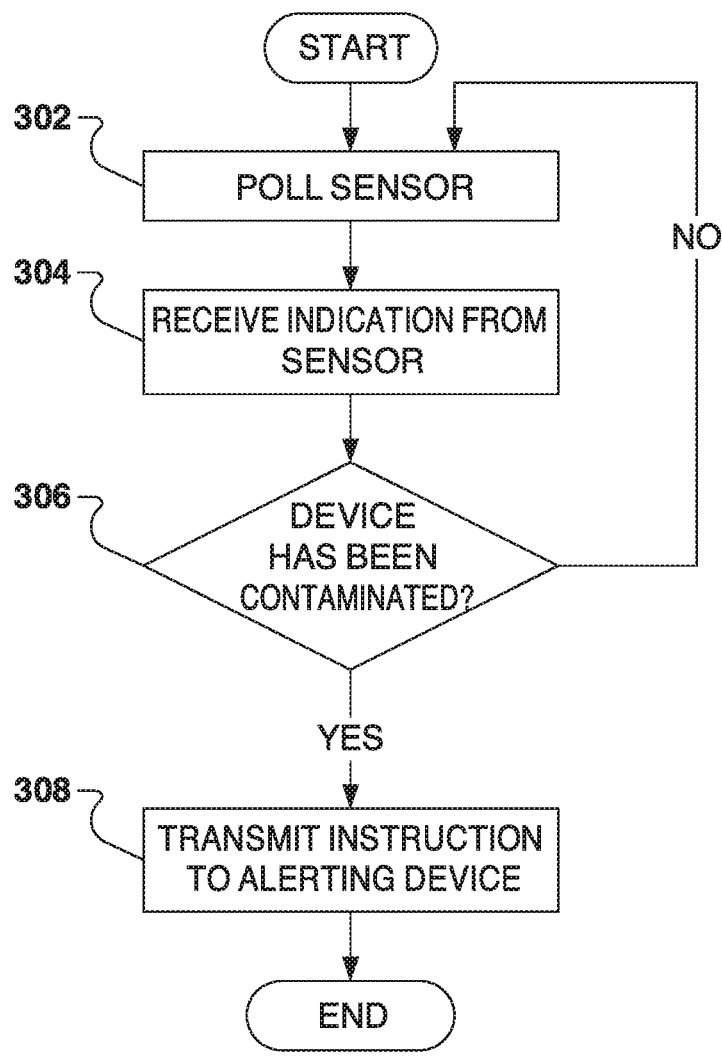
FIG. 3 illustrates example steps in a method of signaling responsive to sensing contamination of the suction regulator device of FIG. 1.

Steps in an example method or algorithm of sensing contamination are illustrated in FIG. 3. The method may, for example, be carried out by the processor on the circuit board 204 of the suction regulator device 100. Initially, the processor may poll (step 302) the sensor 216. Responsive to being polled, the sensor 216 transmits, to the processor, a contamination indication. Upon receiving (step 304) the contamination indication, the processor determines (step 306), from the received contamination indication, whether the suction regulator device 100 has been contaminated. Upon determining (step 306) that the suction regulator device 100 has not been contaminated, the processor returns to the polling step (step 302). Upon determining (step 306) that the suction regulator device 100 has been contaminated, the processor may transmit (step 308) an instruction to an alerting device, instructing the alerting device to generate an alert, thereby indicating to the user that the suction regulator device 100 has been contaminated.

There a many manners in which the sensor 216 may be implemented. In operation, in one example, the light source 218 illuminates the pathway 212. The light sensor 216, located on the opposite side of the pathway 212, measures received light. The light sensor 216 may be initialized with a threshold measurement of light, representative of a predetermined clarity in the pathway 212. Responsive to polling from the processor, the light sensor may obtain a measurement of light, compare the measurement to the threshold and transmit a binary contamination indication to the processor. As a consequence of obtaining a measurement of light that is at or above the threshold, the light sensor 216 may transmit, to the processor, a contamination indication that indicates no contamination. As a consequence of obtaining a measurement of light that is below the threshold, the light sensor 216 may transmit, to the processor, a contamination indication that indicates contamination. Accordingly, a reduction in amount of light received at the light sensor 216 from the light source 218 is associated with a presence of organic matter in the pathway 212.

In one embodiment, the pathway 212 contains features (not shown) designed to collect contaminants. In the presence of such features, the light sensor 216 may be replaced by, or augmented with, a conductivity sensor (not shown). The conductivity sensor may be adapted to measure a conductivity of contaminants collected by the feature designed to collect contaminants.

The conductivity sensor may be initialized with a set point measurement of conductivity, representative of a lack of contaminants in the feature of the pathway 212. Responsive to polling from the processor, the conductivity sensor may obtain a measurement of conductivity, compare the measurement to the set point and transmit a binary contamination indication to the processor. As a consequence of obtaining a measurement of conductivity that is at or below the threshold, the conductivity sensor may transmit, to the processor, a contamination indication that indicates no contamination. As a consequence of obtaining a measurement of conductivity that is above the threshold, the conductivity sensor may transmit, to the processor, a contamination indication that indicates contamination.

There a many manners in which the alerting device may be implemented. The alerting device may, for a few examples, employ an alert that is viewable, an alert that is audible and/or an alert that employs haptic technology. Haptic technology is a tactile feedback technology that relates to the sense of touch and may involve the application of forces, vibrations and/or other motions to a user.

An example viewable alert may be mechanical in nature. For instance, by default, a user may be allowed to view, through a transparent window (not shown) in the cover 106 of the suction regulator device 100, a first strip. The first strip may, for example, be white. Responsive to receiving, from the processor, the instruction, the alerting device may replace the first strip with a second strip, where the color of the second strip is distinct from the color of the first strip. The second strip may, for example, be red. The window through which the strip may be viewed by the user may be anywhere in the cover 106 of the suction regulator device 100.

Alternatively, there may be a bicolor strip, the bicolor strip having a first color and a second color. By default, the window in the cover 106 may allow viewing of only the first color of the bicolor strip. Responsive to receiving the instruction, generating the alert indicative of the contamination may involve causing switching such that the window allows viewing of only the second color of the bicolor strip.

The alerting device may comprise a viewing window whose marking, color or shape changes by a mechanical means. The mechanical means may be, for three examples, a solenoid, a magnetic switch or a motor.

Another example viewable alert may by electronic in nature. For instance, by default, the contamination indicator light 102 may be OFF. Responsive to receiving, from the processor, the instruction, the alerting device may switch ON the contamination indicator light 102. The contamination indicator light 102 may be an incandescent bulb or may be one or more light emitting diodes (LEDs), among other options. Indeed, a liquid crystal display (LCD) screen may also be employed as an alerting device.

Where the contamination indicator light 102 is one or more LEDs, by default, the contamination indicator light 102 may glow green. Responsive to receiving, from the processor, the instruction, the alerting device may switch the contamination indicator light 102 to glow red.

The audible alarm to notify the user that the unit has become contaminated may be heard directly from the device. The audible notification can also be sent from the device to a master nurse station, or to whomever the users would like the notification sent.

Figure 4:
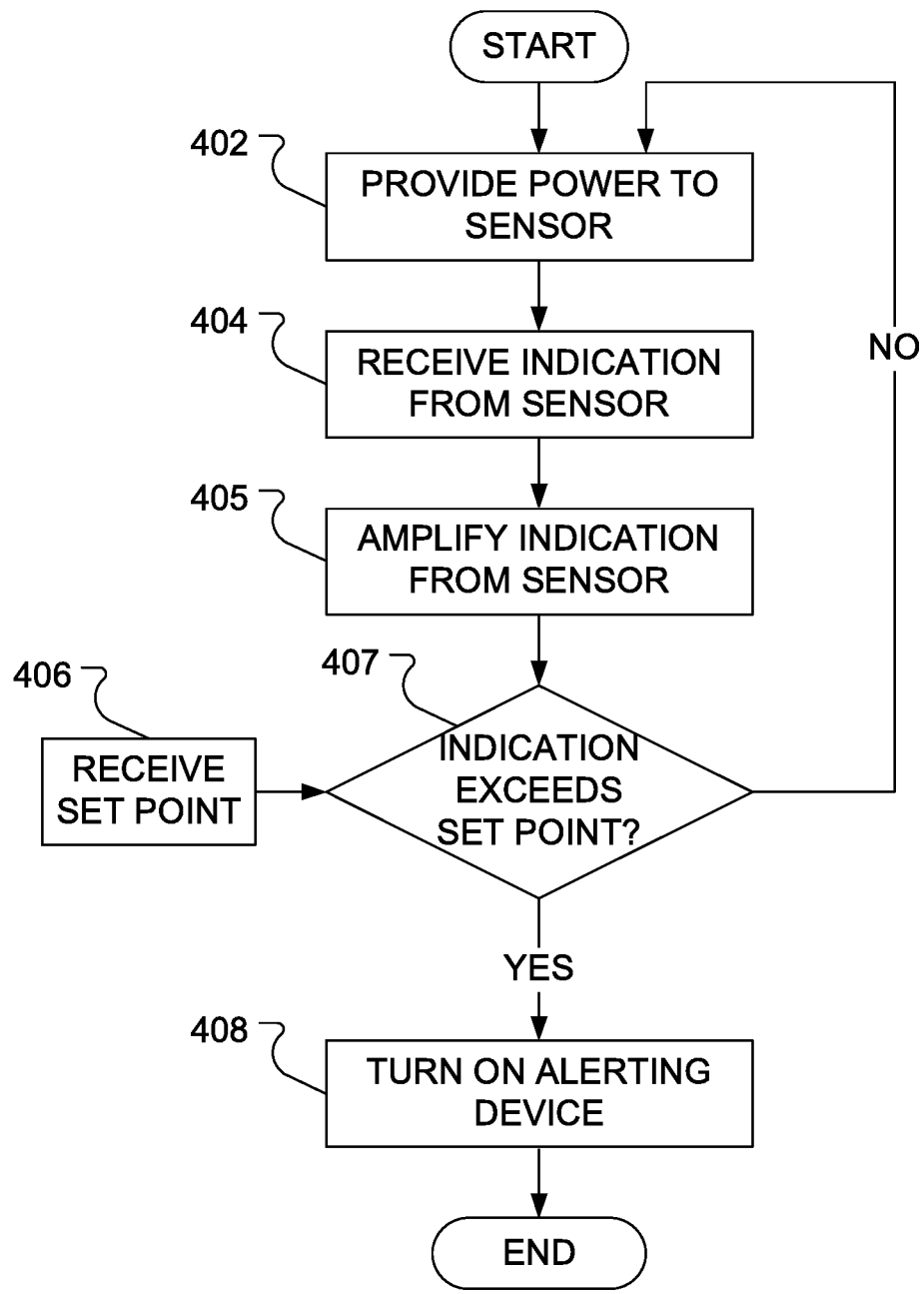
FIG. 4 illustrates example steps in a method of signaling responsive to sensing contamination the suction regulator device of FIG. 1.

FIG. 4 illustrates example steps in a method of signaling responsive to sensing contamination the suction regulator device 100 of FIG. 1. The method may, for example, be carried out by circuitry on the circuit board 204 of the suction regulator device 100. Initially, the circuitry may provide power (step 402) to the sensor 216. Responsive to being polled, the sensor 216 transmits, to the circuitry, a contamination indication. Upon receiving (step 404) the contamination indication, the circuitry amplifies (step 405) the indication. It may be considered that the circuitry receives (step 406) a set point defining a border between contaminated and clean. For simplicity, the set point may be established as a fixed tap on a circuit including one or more resistors. Alternatively, set point may be established as a variable tap on a potentiometer. Responsive to the amplification (step 405) of the indication, the circuitry determines (step 407), from the amplified indication, whether the amplified indication exceeds the set point. Upon determining (step 407) that the amplified indication does not exceed the set point, the circuitry returns to the polling step (step 402). Upon determining (step 407) that the amplified indication exceeds the set point, the circuitry may turn on (step 408) an alerting device, thereby indicating to the user that the suction regulator device 100 has been contaminated.

For completeness, it is noted that instead of, or in addition to, a system that autonomously determines contamination and generates an alert, the suction regulator device 100 may be arranged to allow for an assessment by the user.

In one example, mirrors (not shown) may be installed in the channels 214 with an orientation that reflects light in the channels 214 through a window (not shown) that may be inspected by the user. It is left to the user to, by inspecting the channels 214 through the window, determine whether the suction regulator device 100 has been contaminated.

In another example, an ultraviolet light source (not shown) may be installed in the channels 214 such that any material in the channels 214 may be illuminated and viewed, by the user, through a window (not shown). It is left to the user to, by inspecting the illuminated material (if any) through the window, determine whether the suction regulator device 100 has been contaminated.

In a further example, the entry point 210 may be viewed, by the user, through a window (not shown). The window may be specifically arranged to provide a predetermined magnification to enhance the inspection of the channels by the user. It is left to the user to, by inspecting the entry point 210 through the window, determine whether the suction regulator device 100 has been contaminated.

Notably, existing suction regulator devices may be upgraded to allow for autonomous signaling of contamination and/or user-accomplished contamination inspection.

For one autonomous signaling example, upgrading an existing suction regulator device may begin with disassembly. More particularly, the cover may be removed. Subsequently, an existing circuit board and molded layer may be removed and replaced with the circuit board 204 and the molded layer 206 of FIG. 2. Additionally, if the alerting device is distinct from the circuit board 204 and the molded layer 206, the existing suction regulator device may be adapted to accommodate the alerting device. For example, the existing suction regulator device may be provided with a replacement cover 106 with associated contamination indicator light 102 and/or low battery indicator light 104. Notably, rather than replace the molded layer, upgrading an existing suction regulator device may involve installing a sensor device proximate the pathway in the molded layer of the existing suction regulator device.

For one user-accomplished contamination inspection example, upgrading an existing suction regulator device may begin with disassembly. More particularly, the cover may be removed. Subsequently, the existing suction regulator device may be provided with a replacement cover (not shown). The replacement cover may, for one example, include a transparent window through which the user may inspect channels in a molded layer of the existing suction regulator device. The replacement cover may, for another example, include a transparent window through which the user may inspect the entry point of a molded layer of the existing suction regulator device.

While the cover 106 is illustrated in FIG. 1 as formed of an opaque material, the person of ordinary skill in the art may consider that the cover 106 may be formed of a material that is wholly or partially transparent, thereby obviating a requirement for a transparent window.

Similarly, while the base 202 is illustrated in FIG. 2 as formed of an opaque material, the person of ordinary skill in the art may consider that the base 202 may be formed of a material that is wholly or partially transparent, thereby obviating a requirement for a transparent window for viewing the channels and any contaminants that may have entered into the channels.

The person of ordinary skill in the art will also understand that the molded layer 206 may be formed by other processes, such as a machining process, rather than a molding process.

Furthermore, the molded layer 206 and the base 202 may, optionally, be formed as one, integral piece.

The above-described implementations of the present application are intended to be examples only. Alterations, modifications and variations may be effected to the particular implementations by those skilled in the art without departing from the scope of the application, which is defined by the claims appended hereto.

What is claimed is:

1. A suction regulator device comprising:
a layer defining an entry point, a plurality of channels and a pathway that connects the entry point to the channels, the channels connected to a vacuum terminal of a vacuum supply system:
a sensor and a light source located on either sides of the pathway, wherein the sensor is operable to sense a change in clarity of a gas passing from the entry point to a vacuum terminal by sensing light from the light source;
an alerting device; and a processor adapted to:
receive, from the sensor, an indication;
determine, from the indication, that the suction regulator device has been contaminated;
and transmit, to the alerting device, an instruction to generate an alert indicative of contamination.

2. The suction regulator device of claim 1 wherein the sensor comprises a light sensor adapted to measure an amount of light received from the light source, wherein a change in amount of light received from the light source is associated with a presence of contamination in the pathway.

3. The suction regulator device of claim 2 wherein the light source comprises an incandescent bulb.

4. The suction regulator device of claim 2 wherein the light source comprises a light emitting diode.

5. The suction regulator device of claim 2 further comprising an optical filter between the light sensor and the light source.

6. The suction regulator device of claim 5 wherein the optical filter comprises a polarizing filter.

7. The suction regulator device of claim 1 wherein the pathway contains features to collect contaminants.

8. The suction regulator device of claim 7 wherein the sensor comprises a conductivity sensor adapted to measure a conductivity of the contaminants.

9. The suction regulator device of claim 1 wherein the alerting device comprises a contamination indicator light.

10. The suction regulator device of claim 9 wherein the contamination indicator light comprises an incandescent bulb.

11. The suction regulator device of claim 9 wherein the contamination indicator light comprises a light emitting diode.

12. The suction regulator device of claim 1 wherein the alerting device comprises a device operable to produce an alert that is audible.

13. The suction regulator device of claim 1 wherein the alerting device comprises a device operable to produce an alert that employs haptic technology.

14. A method of retrofitting a suction regulator device, the suction regulator device having a layer defining an entry point, a plurality of channels and a pathway that connects the entry point to the channels, the channels connected to a vacuum terminal of a vacuum supply system, the method comprising:
installing a sensor and a light source located on either sides of the pathway, wherein the sensor is operable to sense a change in clarity of a gas passing from the entry point to vacuum terminal by sensing light from the light source;
installing an alerting device; and installing a processor adapted to:
receive, from the sensor, an indication;
determine, from the indication, that the suction regulator device has been contaminated;
and transmit, to the alerting device, an instruction to generate an alert indicative of the contamination.

* * * * *